United States Patent [19]

Nishikawa et al.

[11] Patent Number: 5,245,070

[45] Date of Patent: Sep. 14, 1993

[54] ALKYL PHOSPHATES HAVING A BRANCHED ALKYL GROUP

[75] Inventors: Naoyuki Nishikawa; Hideto Mori, both of Minami-ashigara, Japan

[73] Assignee: Fuji Photo Film Co., Ltd., Kanagawa, Japan

[21] Appl. No.: 847,186

[22] Filed: Mar. 6, 1992

[30] Foreign Application Priority Data

Mar. 11, 1991 [JP] Japan .................................. 3-045042

[51] Int. Cl.$^5$ .......................... C09F 9/09; C09F 9/11
[52] U.S. Cl. ................................ 558/208; 558/210; 252/49.8; 252/89.1; 252/DIG. 17; 252/DIG. 1; 252/358; 252/352; 252/331; 252/363.5; 252/400.2; 252/510; 106/2
[58] Field of Search ............................... 558/208, 210

[56] References Cited

U.S. PATENT DOCUMENTS

| | | | |
|---|---|---|---|
| 2,005,619 | 6/1935 | Graves | 558/210 X |
| 2,694,689 | 11/1954 | Gamrath et al. | 558/210 X |
| 2,739,978 | 3/1956 | Gamrath et al. | 558/210 X |
| 3,168,554 | 2/1965 | Phillips et al. | 558/208 X |
| 3,238,277 | 3/1966 | Sigan et al. | 558/208 |
| 4,039,636 | 8/1977 | Claus et al. | 558/208 |

FOREIGN PATENT DOCUMENTS

0740078 11/1955 United Kingdom ................ 558/210

OTHER PUBLICATIONS

Chemical Abstracts, 83318k, vol. 80, 1974; "Synthesis and Acid Hydrolysis of Monophosphate and Pyrophosphate Esters of Phytanol and Phytol", C. N. Joo et al. Can. J. Biochem, 51 (11), 1527-1536 (1973).

C. N. Joo et al., "Synthesis and Acid Hydrolysis of Monophosphate and Pyrophosphate Esters of Phytanol and Phytol", Can. J. Biochem, 51 (11), pp. 1527 to 1536 (1973).

Gamrath et al. IV, Ind. Eng. Chem., vol. 46, No. 1, pp. 208 to 212 (1954).

Primary Examiner—Floyd D. Higel
Attorney, Agent, or Firm—Sughrue, Mion, Zinn, Macpeak & Seas

[57] ABSTRACT

A compound represented by the following general formula I;

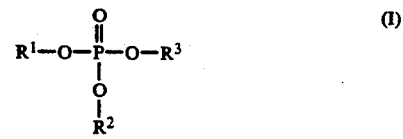

wherein $R^1$, $R^2$ and $R^3$ independently represent a hygrogen atom, alkyl group or aryl group, provided that at least one of $R^1$, $R^2$ and $R^3$ represents 3,7,11,15-tetramethylhexadecyl group, 3,7,11-trimethyldodecyl group or 3,7-dimethyloctyl group, or a salt thereof. The compound may have R- or S- configuration with respect to each asymmetric carbon contained therein and it may be present as a racemate. The compounds of the present invention are useful as surfactants, lubricants, dispersants, emulsifiers, additives, stabilizers, solubilizers, water-repellants, antistatic agents and the like.

4 Claims, No Drawings

ALKYL PHOSPHATES HAVING A BRANCHED ALKYL GROUP

BACKGROUND OF THE INVENTION

The present invention relates to novel alkyl phosphates having a branched alkyl group, which are useful as surfactants, lubricants, dispersants, emulsifiers, additives, stabilizers, solubilizers, water-repellants, antistatic agents and the like.

Hitherto, trialkyl phosphate compounds have been widely used as additives such as plastisizers and stabilizers, lubricants, dispersants or the like. Most of trialkyl phosphate compounds used as plastisizers are higher alkyl phosphates in view of volatility and water-solubility of the compounds. Typical examples of such alkyl phosphates include trioctyl phosphate, tributoxyethyl phosphate, triphenyl phosphate and octyldiphenyl phosphate. Triaryl phosphates are more advantageous as plastisizers, but they have a problem of low-temperature resistance.

Dialkyl phosphates and monoalkyl phosphates are generally used as surfactants. The alkyl phosphate surfactants are used, for instance, as wetting agents such as disclosed in R. Oda et al., "Surfactants and Applications thereof", Maki Shoten, p98, (1957), collecting property improving agents for fibers such as disclosed in Japanese Patent Application Laying-open (KOKAI) (referred to as "J.P. KOKAI" hereinafter) No. Sho 47-39788, antistatic agents such as disclosed in Japanese Patent Publication (KOKOKU) No. Sho 42-11480 and softening agents. Alkyl phosphates having a branched alkyl group, in particular, are known to be useful as lubricants for treating fibers such as disclosed in J.P. (KOKAI) No. Sho 48-19892.

While various alkyl phosphate compounds have been developed and practically used as described above, it is still sought to improve the various properties of the alkyl phosphates.

On the other hand, it has been known that cell membranes of archaebacteria are composed of glycerolipids having a hydrophobic group comprising linear isoprenoids bonded with ether bonds. Recently, in investigations of the functions of cell membranes of archaebacteria and application thereof for liposomes, reported was synthesized glycerophospholipids having isoprenoid side chains, which imitate the lipids constituting the cell membranes of archaebacteria (Yamauchi et al., J. Am. Chem. Soc., 112, p3188 (1990); Toda et al., Preprints for Spring Conference (1990) of the Chemical Society of Japan, p1793). As a result of these investigations, it was found that these glycerophospholipids having isoprenoid side chains have a low phase transition point and that the lipid bilayer membrane constituted by the glucerophospholipids has an excellent barrier property.

Further, also known were lipid bilayer membranes and lipid-bilayer-membrane-immobilized polymer films utilizing quaternary ammonium salts having isoprenoid chains as disclosed in J.P. (KOKAI) No. Hei 2-288849 and it was found that those lipid bilayer membranes have fluidity similar to that of biological membranes as well as excellent flexibility and strength. However, any alkyl phosphate having isoprenoid side chains, which may be suitably used as surfactants and dispersants, is not reported.

SUMMARY OF THE INVENTION

In view of the circumstances described above, an object of the present invention is to provide alkyl phosphates having excellent stability, solubilizing property, dispersibility and low temperature resistance.

The above-described object of the invention has been achieved by a discovery of compounds represented by the following general formula I and salts thereof.

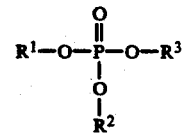

In the general formula I, $R^1$, $R^2$ and $R^3$ independently represent a hygrogen atom, alkyl group or aryl group, provided that at least one of $R^1$, $R^2$ and $R^3$ represents 3,7,11,15-tetramethylhexadecyl group (phytanyl group), 3,7,11-trimethyldodecyl group or 3,7-dimethyloctyl group. The compounds may have either of R or S-configuration with respect to each asymmetric carbon contained therein.

DESCRIPTION OF THE PREFERRED EMBODIMENTS

The novel compounds according to the present invention are the alkyl phosphates represented by the above general formula I and the salts thereof.

Preferred examples of the alkyl group include butyl, hexyl, octyl, 2-ethylhexyl and the like. Preferred examples of the aryl group include phenyl.

As regards the stereochemistry of the compounds, they may have R- or S-configuration with respect to each asymmetric carbon contained therein and they may be present as racemates.

Preferred salts of the compounds according to the present invention are alkali metal and alkaline earth metal salts.

The compounds of the present invention are, in other words, tri-, di- and monoalkyl phosphates at least one of which alkyl chains is an isoprenoid chain.

The alkyl phosphates of the present invention may be prepared by a conventional method for preparing alkyl phosphates, namely, by reacting phosphorous oxychloride with an alcohol corresponding to the alkyl group under a basic condition or by introducing hydroxyl groups with equivalent amount of water after the reaction of phosphorous oxychloride and alcohol. Alternatively, they may be prepared by reacting a phosphorylating agent such as phenyl phosphorodichloridate, methyl phosphorodichloridate, bromoethyl phosphorodichloridate and diphenyl phosphorochloridate with an alcohol corresponding to the alkyl group under a basic condition and then deprotecting.

Most of the alkyl phosphates of the present invention can be obtained as an oily product in spite of the large carbon number thereof and have a significantly lower melting point as compared with a corresponding alkyl phosphates having linear alkyl chain with the same carbon number. In addition, the alkyl phosphates of the present invention exhibit extremely excellent dispersibility. Hence, the alkyl phosphates of the present invention are useful as surfactants, lubricants, dispersants, emulsifiers, additives, stabilizers, solubilizers, water-repellants, antistatic agents and the like. In particular, the alkyl phosphates of he present invention are useful as dispersants because of the excellent dispersibility thereof. Further, thanks to the low melting points of the compounds, they hardly precipitate in use thereof, for instance, as lubricants.

The present invention is hereinafter explained more in detail by reference to the following non limitative examples.

EXAMPLE 1

Synthesis of 3RS,7R,11R,15 tetramethylhexadecanol (7R,11R)-phytol (200 g) was dissolved in ethanol (1000 ml), added with platinum oxide (1 g) and stirred for 6 hours at room temperature under hydrogen atmosphere. After the completion of the reaction, insoluble material was removed by filtration through a Celite layer and the filtrate was concentrated under reduced pressure to obtain 201 g of 3RS,7R,11R,15tetramethylhexadecanol ((3RS, 7R,11R)-phytanol).

EXAMPLE 2

Synthesis of 3,7,11-trimethyldodecanol

Farnesol (200 g) was dissolved in ethanol (1000 ml), added with platinum oxide (1 g) and stirred for 24 hours at room temperature under hydrogen atmosphere. After the completion of the reaction, insoluble material was removed by filtration through a Celite layer and the filtrate was concentrated under reduced pressure to obtain 3,7,11-trimethyldodecanol (195 g).

EXAMPLE 3

Synthesis of 3,7-dimethyloctanol

Geraniol (100 g) was dissolved in ethanol (500 ml), added with platinum oxide (500 mg) and stirred for 24 hours at room temperature under hydrogen atmosphere. After the completion of the reaction, insoluble material was removed by filtration through a Celite layer and the filtrate was concentrated under reduced pressure to obtain 3,7-dimethyloctanol (100 g).

EXAMPLE 4

Synthesis of tri(3RS,7R,11R,15-tetramethylhexadecyl) phosphate

Phosphorous oxychloride (200 g) was dissolved in dichloromethane (100 ml), added with a solution of 3RS,7R,11R,15 tetramethylhexadecanol (8.94 g), triethylamine (3.0 g) and N,N-dimethylaminopyridine (200 mg) in dichloromethane (50 ml) dropwise and stirred for 24 hours. After washing the reaction mixture with water and then with 10% aqueous solution of citric acid, the organic layer was dried over anhydrous sodium sulfate and the dichloromethane was evaporated under reduced pressure. Resulted residue was purified by silica gel chromatography and fractions of hexane/ethyl acetate=97/3 were collected to obtain tri(3RS,7R,11R,15-tetramethylhexadecyl) phosphate (6.8 g).

IR Spectra (neat) cm$^{-1}$: 2960, 2925, 2870, 1460, 1380, 1290, 1270, 1150, 1140, 1000, 920
FAB-MASS: (M+H)+939

EXAMPLE 5

Synthesis of tri(3,7,11-trimethyldodecyl) phosphate

By using 3,7,11-trimethyldodecanol, tri(3,7,11-trimethyldodecyl) phosphate was obtained in the same manner as used in Example 4.

IR Spectra (neat) cm$^{-1}$: 2960, 2925, 2870, 1460, 1380, 1290, 1270, 1150, 1140, 1000, 920
FAB-MASS (M+H)+729

EXAMPLE 6

Synthesis of tri(3,7-dimethyloctyl) phosphate

By using 3,7-dimethyloctanol, tri(3,7-dimethyloctyl) phosphate was obtained in the same manner as used in Example 4.

IR Spectra (neat) cm$^{-1}$: 2960, 2925, 2870, 1460, 1380, 1290, 1270, 1150, 1140, 1000, 920
FAB-MASS: (M+H)+519

EXAMPLE 7

Synthesis of di(3RS,7R,11R,15-tetramethylhexadecyl)phenyl phosphate

Phenyl phosphorodichloridate (6.3 g) was dissolved in dichloromethane (100 ml), added with a solution of 3RS,7R,11R,15-tetramethylhexadecanol (18 g), triethylamine (6.1 g) and N,N-dimethylaminopyridine (200 mg) in dichloromethane (50 ml) dropwise and stirred for 24 hours. After washing the reaction mixture with 10% aqueous solution of citric acid and then with saturated aqueous solution of sodium hydrogen carbonate, the organic layer was dried over anhydrous sodium sulfate and the dichloromethane was evaporated under reduced pressure. Resulted residue was purified by silica gel chromatography and fractions of hexane/ethyl acetate=95/5 were collected to obtain di(3RS,7R,11R,15-tetramethylhexadecyl) phenyl phosphate (15 g).

IR Spectra (neat) cm$^{-1}$: 3060, 2960, 2925, 2870, 1600, 1495, 1460, 1380, 1290, 1220, 1160, 1050, 950, 760, 690
FAB-MASS: (M+H)+735

EXAMPLE 8

Synthesis of di(3,7,11-trimethyldodecyl)phenyl phosphate

By using 3,7,11-trimethyldodecanol, di(3,7,11-trimethyldodecyl)phenyl phosphate was obtained in the same manner as used in Example 7.

IR Spectra (neat) cm$^{-1}$: 3060, 2960, 2925, 2870, 1600, 1495, 1460, 1380, 1290, 1220, 1160, 1050, 950, 760, 690
FAB-MASS (M+H)+595

EXAMPLE 9

Synthesis of di(3,7-dimethyloctyl)phenyl phosphate

By using 3,7-dimethyloctanol, di(3,7-dimethyloctyl)phenyl phosphate was obtained in the same manner as used in Example 7.

IR Spectra (neat) cm$^{-1}$: 3060, 2960, 2925, 2870, 1600, 1495, 1460, 1380, 1290, 1220, 1160, 1050, 950, 760, 690
FAB-MASS: (M+H)+455

EXAMPLE 10

Synthesis of 3RS,7R,11R,15-tetramethylhexadecyldiphenyl phosphate

Diphenyl phosphorochloridate (13.4 g) was dissolved in dichloromethane (100 ml), added with a solution of 3RS,7R,11R,15-tetramethylhexadecanol (14.9 g), triethylamine (4.04 g) and N,N-dimethylaminopyridine (200 mg) in dichloromethane (50 ml) dropwise and stirred for 24 hours. After washing the reaction mixture with 10% aqueous solution of citric acid and then with saturated aqueous solution of sodium hydrogen carbonate, the organic layer was dried over anhydrous sodium sulfate and the dichloromethane was evaporated under reduced pressure. Resulted residue was purified by silica gel chromatography and fractions of hexane/ethyl acetate=95/5 were collected to obtain 3RS,7R,11R,15-tetramethylhexadecyldiphenyl phosphate (27 g).

IR Spectra (neat) cm$^{-1}$: 3060, 2960, 2925, 2870, 1600, 1495, 1460, 1380, 1290, 1220, 1190, 1160, 1050, 950, 750, 690

FAB-MASS: (M+H)$^+$531

EXAMPLE 11

Synthesis of 3,7,11-trimethyldodecyldiphenyl phosphate

By using 3,7,11-trimethyldodecanol, 3,7,11-trimethyldodecyldiphenyl phosphate was obtained in the same manner as used in Example 7.

IR Spectra (neat) cm$^{-1}$: 3060, 2960, 2925, 2870, 1600, 1495, 1460, 1380, 1290, 1220, 1190, 1160, 1050, 950, 750, 690

FAB-MASS: (M+H)$^+$461

EXAMPLE 12

Synthesis of 3,7-dimethyloctyldiphenyl phosphate

By using 3,7-dimethyloctanol, 3,7-dimethyloctyldiphenyl phosphate was obtained in the same manner as used in Example 7.

IR Spectra (neat) cm$^{-1}$: 3060, 2960, 2925, 2870, 1600, 1495, 1460, 1380, 1290, 1220, 1190, 1160, 1050, 950, 750, 690

FAB-MASS (M+H)$^+$391

EXAMPLE 13

Synthesis of di(3RS,7R,11R,15-tetramethylhexadecyl) phosphate

Di(3RS,7R,11R,15-tetramethylhexadecyl)phenyl phosphate (15 g) was dissolved in a mixture of methanol, ethyl acetate and acetic acid (5/5/1, 120 ml) and added with platinum dioxide (300 mg) to carry out hydrogenolysis for 2 days. After the completion of the reaction, insoluble material was removed by filtration through a Celite layer and the filtrate was concentrated under reduced pressure to obtain di(3RS,7R,11R,15-tetramethylhexadecyl) phosphate (12.5 g).

IR Spectra (neat) cm$^{-1}$: 2960, 2925, 2870, 1460, 1380, 1220, 1190, 1020, 920, 740

FAB MASS: (M+H)$^+$659

EXAMPLE 14

Synthesis of di(3,7,11-trimethyldodecyl) phosphate

By using di(3,7,11-trimethyldodecyl)phenyl phosphate, di(3,7,11-trimethyldodecyl) phosphate was obtained in the same manner as used in Example 13.

IR Spectra (neat) cm$^{-1}$: 2960, 2925, 2870, 1460, 1380, 1220, 1190, 1020, 920, 740

FAB-MASS: (M+H)$^+$519

EXAMPLE 15

Synthesis of di(3,7-dimethyloctyl) phosphate

By using di(3,7-dimethyloctyl)phenyl phosphate, di(3,7-dimethyloctyl) phosphate was obtained in the same manner as used in Example 13.

IR Spectra (neat) cm$^{-1}$: 2960, 2925, 2870, 1460, 1380, 1220, 1190, 1020, 920, 740

FAB-MASS: (M+H)$^+$379

EXAMPLE 16

Synthesis of 3RS,7R,11R,15-tetramethylhexadecyl phosphate

3RS,7R,11R,15-tetramethylhexadecyldiphenyl phosphate (27 g) was dissolved in acetic acid (200 ml) and added with platinum dioxide (300 mg) to carry out hydrogenolysis for 2 days. After the completion of the reaction, insoluble material was removed by filtration through a Celite layer and the filtrate was concentrated under reduced pressure to obtain 3RS,7R,11R,15-tetramethylhexadecyl phosphate (14.0 g).

IR Spectra (neat) cm$^{-1}$: 2960, 2925, 2870, 1460, 1380, 1150, 1030

FAB MASS: (M+H)$^+$379

EXAMPLE 17

Synthesis of 3,7,11-trimethyldodecyl phosphate

By using 3,7,11-trimethyldodecyldiphenyl phosphate, 3,7,11-trimethyldodecyl phosphate was obtained in the same manner as used in Example 16.

IR Spectra (neat) cm$^{-1}$: 2960, 2925, 2870, 1460, 1380, 1150, 1030 FAB-MASS: (M+H)$^+$309

EXAMPLE 18

Synthesis of 3,7-dimethyloctyl phosphate

By using 3,7-dimethyloctyldiphenyl phosphate, 3,7-dimethyloctyl phosphate was obtained in the same manner as used in Example 16.

IR Spectra (neat) cm$^{-1}$: 2960, 2925, 2870, 1460, 1380, 1150, 1030

FAB-MASS: (M+H)$^+$239

EXAMPLE 19

Synthesis of 3RS,7R,11R,15-tetramethylhexadecylphenyl phosphate

3RS,7R,11R,15-tetramethylhexadecyldiphenyl phosphate (27 g) was dissolved in ethyl acetate (200 ml) and added with platinum dioxide (300 mg) to carry out hydrogenolysis for a day. After the completion of the reaction, insoluble material was removed by filtration through a Celite layer and the filtrate was concentrated under reduced pressure. The residue was purified by silica gel chromatography (chloroform/methanol=8/2) to obtain 3RS,7R,11R,15-tetramethylhexadecylphenyl phosphate (12.8 g).

IR Spectra (neat) cm$^{-1}$: 2960, 2925, 2870, 1600, 1490, 1460, 1380, 1200, 1030, 950, 770, 690

FAB-MASS: (M+H)$^+$455

What is claimed is:

1. A compound represented by the following formula (I):

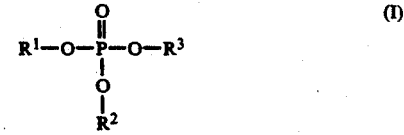

wherein $R^1$ and $R^2$ independently represent a 3,7,11,15-tetramethylhexadecyl group or 3,7,11-trimethyldodecyl group, or a salt thereof.

2. The compound of claim 1, which is di(3RS,7R,11R,15-tetramethylhexadecyl) phosphate or a salt thereof.

3. The compound of claim 1, which is di(3R,7R,11R,15-tetramethylhexadecyl) phosphate or a salt thereof.

4. The compound of claim 1, which is di(3,7,11-tetramethylhexadecyl) phosphate or a salt thereof.

* * * * *